US012727834B2

(12) United States Patent
Mirzaei et al.

(10) Patent No.: US 12,727,834 B2
(45) Date of Patent: Sep. 8, 2026

(54) HIGH EFFICIENCY POWER DISTRIBUTION UNIT FOR A MEDICAL IMAGING SYSTEM

(71) Applicant: GE Precision Healthcare LLC, Waukesha, WI (US)

(72) Inventors: Saeid Mirzaei, Muskego, WI (US); Nicolas Levilly, Magny les Mameaux (FR); Dominique Poincloux, Senlisse (FR); Loic Cabrol, Gif sur Yvette (FR); Hexin Guo, Beijing (CN); Xuyong Yang, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 100 days.

(21) Appl. No.: 18/678,211

(22) Filed: May 30, 2024

(65) Prior Publication Data

US 2025/0366799 A1 Dec. 4, 2025

(51) Int. Cl.

| | |
|---|---|
| ***A61B 6/03*** | (2006.01) |
| ***A61B 6/00*** | (2006.01) |
| ***A61B 6/04*** | (2006.01) |
| ***A61B 6/42*** | (2024.01) |
| ***H02M 1/15*** | (2006.01) |

(Continued)

(52) U.S. Cl.

CPC ............ *A61B 6/032* (2013.01); *A61B 6/0487* (2020.08); *A61B 6/4266* (2013.01); *A61B 6/4435* (2013.01); *H02M 1/15* (2013.01); *H02M 1/4233* (2013.01); *H02M 7/05* (2021.05)

(58) Field of Classification Search

CPC ..... A61B 6/032; A61B 6/0487; A61B 6/4266; A61B 6/4435; H02M 7/05; H02M 1/15; H02M 1/4233

See application file for complete search history.

(56) References Cited

U.S. PATENT DOCUMENTS

| | | | | |
|---|---|---|---|---|
| 5,808,376 A * | 9/1998 | Gordon | G01T 1/175 | 307/64 |
| 9,031,198 B2 * | 5/2015 | Roos | H05G 1/12 | 378/101 |
| 9,595,883 B2 | 3/2017 | Nieberlein et al. | | |

(Continued)

FOREIGN PATENT DOCUMENTS

| | | | |
|---|---|---|---|
| EP | 4300767 A | 1/2024 | |
| WO | WO-2024049988 A1 * | 3/2024 | A61B 6/56 |

OTHER PUBLICATIONS

Three-Phase PFC Rectifier and High-Voltage Generator for X-Ray Systems (Year: 2017).*

(Continued)

*Primary Examiner* — Uzma Alam
*Assistant Examiner* — Fani Polyzos Boosalis
(74) *Attorney, Agent, or Firm* — Fletcher Yoder, P.C.

(57) ABSTRACT

A medical imaging system includes an X-ray source configured to emit X-rays. The medical imaging system also includes a high voltage generator configured to provide power to the X-ray source. The medical imaging system further includes a high efficiency power distribution unit configured to receive electrical power from an electrical grid and to store the electrical power, wherein the high efficiency power distribution unit includes an active rectifier configured to regulate a high voltage direct current outputted to components of the medical imaging system including the high voltage generator.

18 Claims, 10 Drawing Sheets

(51) Int. Cl.
*H02M 1/42* (2007.01)
*H02M 7/04* (2006.01)

(56) References Cited

U.S. PATENT DOCUMENTS 10,646,192 B2 5/2020 Shanthakumar et al.
2015/0055750 A1* 2/2015 Takahashi ............. H01J 35/025 378/104
2015/0085969 A1* 3/2015 Mekonnen ............... H05G 1/10 378/4

OTHER PUBLICATIONS

Leibl, "Three-Phase PFC Rectifier and High-Voltage Generator for X-Ray Systems," 2017, 241 pgs.
EP application 25174298.7 filed May 5, 2025—extended Search Report issued Oct. 22, 2025; 8 pages.

* cited by examiner

| | 20 | 40 | 60 | 80 | 100 | 120 |
|---|---|---|---|---|---|---|
| HEPDU | 704.462 | 699.324 | 694.186 | 689.048 | 683.91 | 678.772 |
| Conv. PDU | 642.706 | 630.922 | 619.138 | 607.354 | 595.57 | 583.786 |

HIGH EFFICIENCY POWER DISTRIBUTION UNIT FOR A MEDICAL IMAGING SYSTEM

BACKGROUND

The subject matter disclosed herein relates to imaging systems and, more particularly, to a high efficiency power distribution unit for a medical imaging system.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In CT imaging systems, a detector array, including a series of detector elements, produces similar signals through various positions as a gantry is displaced around a patient.

A typical CT imaging system draws utility power whenever there is a patient to be scanned. The output high voltage direct current (HVDC) voltage on current power distribution units for a CT imaging system or on the gantry of the CT imaging system is not regulated. This results in huge utility sag voltage during the heavy X-ray shot on HVDC terminals, the X-ray tube, axial motor drive, and any other equipment connected to the direct current (DC) power. In addition, the switching parts of the X-ray generator, such as the insulated-gate bipolar transistor (IGBT), metal-oxide-semiconductor field-effect transistor (MOSFET), and silicon carbide (SiC) MOSFET, need to pass more current to deliver enough power to the X-ray tube, which creates more heat and power dissipation. Further, the three-phase input currents on current power distribution units are distorted or have harmonic current, especially at heavy X-ray shot, which results in the current power distribution units having a lower power factor (e.g., around 0.85).

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a medical imaging system is provided. The medical imaging system includes an X-ray source configured to emit X-rays. The medical imaging system also includes a high voltage generator configured to provide power to the X-ray source. The medical imaging system further includes a high efficiency power distribution unit configured to receive electrical power from an electrical grid and to store the electrical power, wherein the high efficiency power distribution unit includes an active rectifier configured to regulate a high voltage direct current outputted to components of the medical imaging system including the high voltage generator.

In another embodiment, a high efficiency power distribution unit for a medical imaging system including an X-ray source configured to emit X-rays is provided. The high efficiency power distribution unit includes an active rectifier configured to regulate a high voltage direct current outputted to components of the medical imaging system including a high voltage generator configured to provide power to the X-ray source. The active rectifier is configured to enable the high efficiency power distribution unit to output a constant high voltage direct current. The high efficiency power distribution unit is configured to receive electrical power from an electrical grid and to store the electrical power.

In a further embodiment, a method for regulating use of electrical power by a medical imaging system including an X-ray source configured to emit X-rays is provided. The method includes receiving, at a high efficiency power distribution unit for the medical imaging system, three-phase alternating current power from an electrical grid. The method also includes outputting, from the high efficiency power distribution unit, a constant high voltage direct current to components of the medical imaging system including a high voltage generator configured to provide power to the X-ray source, wherein the high efficiency power distribution unit comprises an active rectifier that regulates the high voltage direct current, wherein the active rectifier comprises a passive three-phase diode bridge and two capacitors in a three-phase Vienna rectifier topology.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

Figure 1:
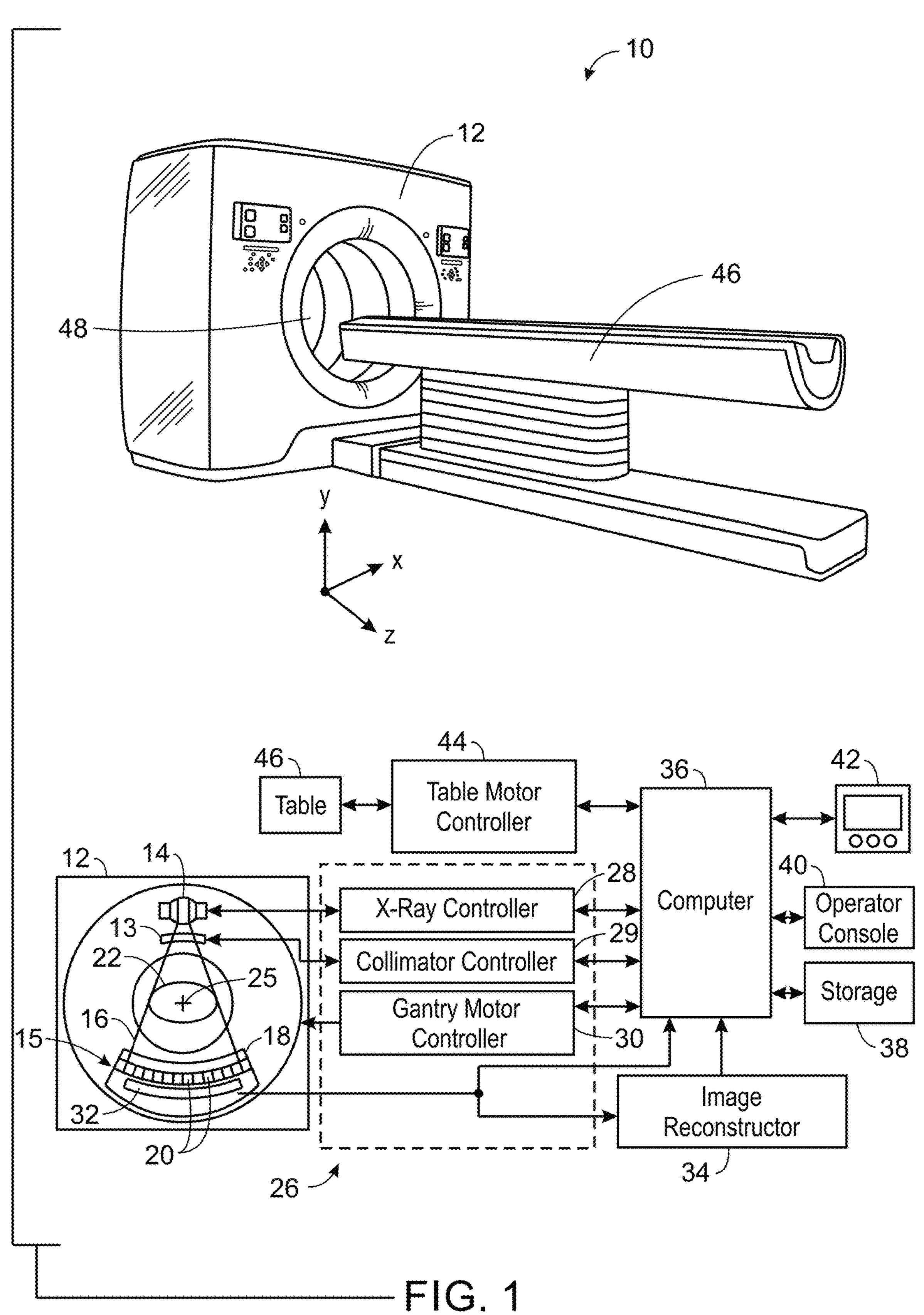
FIG. 1 is a combined pictorial view and block diagram of a computed tomography (CT) imaging system as discussed herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where an X-ray source is utilized.

The present disclosure provides embodiments for high efficiency power distribution unit for a medical imaging system including an X-ray source configured to emit X-rays. The medical imaging system may be a computed tomography imaging system, a fluoroscopy imaging system, and a radiography imaging system (i.e., conventional imaging system including a mammography imaging system). Although discussed in the context of medical imaging, the high efficiency power distribution unit may be utilized with electric vehicles, energy storage, battery chargers, and other applications.

The high efficiency power distribution unit includes an active rectifier that enables the high efficiency power distribution unit to output a constant and stabilized voltage that can be regulated. In particular, active rectifier enables the high efficiency power distribution unit to regulate HVDC voltage (e.g., DC bus voltage) at all conditions (e.g., utility sag voltage, low line condition, heavy X-ray shot, and at maximum gantry speed). This enables the sizes of switches and heat sink to be reduced for the components of the medical imaging system including a high voltage generator configured to provide power to the X-ray source. In addition, this increases the efficiency of the X-ray generator inverter. Further, this enables the manufacturing of a much smaller and cheaper (e.g., approximately 30 percent less) X-ray generator. Since the high efficiency power distribution unit can regulate all HVDC voltage on the terminals of the high efficiency power distribution unit terminals and the DC bus voltage is regulated, a power pan of the medical imaging system may no longer need an advanced Axial Boost Converter (ABC) board.

The use of the active rectifier by the high efficiency power distribution unit also enables the power factor (e.g., ratio of working power (measured in kilowatts (KW)) to apparent power or demand (measured in kilovolt amperes)) of the high efficiency power distribution unit to be close to 1.0 (e.g., 0.99 or greater) at all conditions (e.g., high power condition). In particular, the absence of a harmonic current enables the high efficiency power distribution unit to be more efficient. This results in a reduction in the site utility power range and an increase in cost savings (e.g., due to energy saving). Also, the efficiency of the medical imaging system (e.g., computed tomography imaging system) is increased. The higher power factor also either enables a smaller Mains plug rating or higher available power.

The high efficiency power distribution unit also includes a digital control board configured for online power monitoring. The digital control board is also configured for performing diagnostics offline or remotely if there is any issue on the high efficiency power distribution unit or with the active rectifier.

The disclosed embodiments include an imaging system including an X-ray source configured to emit X-rays. The medical imaging system also includes a high voltage generator configured to provide power to the X-ray source. The medical imaging system further includes a high efficiency power distribution unit configured to receive electrical power from an electrical grid and to store the electrical power, wherein the high efficiency power distribution unit includes an active rectifier configured to regulate a high voltage direct current outputted to components of the medical imaging system including the high voltage generator.

The disclosed embodiments also include a high efficiency power distribution unit for a medical imaging system including an X-ray source configured to emit X-rays is provided. The high efficiency power distribution unit includes an active rectifier configured to regulate a high voltage direct current outputted to components of the medical imaging system including a high voltage generator configured to provide power to the X-ray source. The active rectifier is configured to enable the high efficiency power distribution unit to output a constant high voltage direct current. The high efficiency power distribution unit is configured to receive electrical power from an electrical grid and to store the electrical power.

In certain embodiments, the active rectifier is configured to enable the high efficiency power distribution unit to output a constant high voltage direct current. In certain embodiments, the active rectifier includes a passive three-phase diode bridge and two capacitors. In certain embodiments, the active rectifier includes a three-phase Vienna rectifier topology. In certain embodiments, the active rectifier is configured to regulate the high voltage direct current provided to the high voltage generator under all conditions. In certain embodiments, the conditions include utility sag voltage, low line condition, heavy X-ray shot, and at maximum gantry speed. In certain embodiments, the high efficiency power distribution unit has a power factor of 0.99 or greater at all conditions. In certain embodiments, the active rectifier is communicatively coupled to a controller on the medical imaging system to enable the controller both to monitor and to diagnose any issues with the high efficiency power distribution unit. In certain embodiments, the active rectifier is communicatively coupled to the controller via an Ethernet connection. In certain embodiments, the medical imaging system includes a computed tomography imaging system.

The disclosed embodiments further include a method for regulating use of electrical power by a medical imaging system including an X-ray source configured to emit X-rays. The method includes receiving, at a high efficiency power distribution unit for the medical imaging system, three-phase alternating current power from an electrical grid. The method also includes outputting, from the high efficiency power distribution unit, a constant high voltage direct current to components of the medical imaging system including a high voltage generator configured to provide power to the X-ray source, wherein the high efficiency power distribution unit comprises an active rectifier that regulates the high voltage direct current, wherein the active rectifier comprises a passive three-phase diode bridge and two capacitors in a three-phase Vienna rectifier topology.

With the preceding in mind and referring to FIG. 1, a computed tomography (CT) imaging system 10 is shown, by way of example. The CT imaging system 10 includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 (e.g., patient table) to position subject 22 and gantry 12. Particularly, table 46 moves portions of subject 22 through a gantry opening or bore 48.

Figure 2:
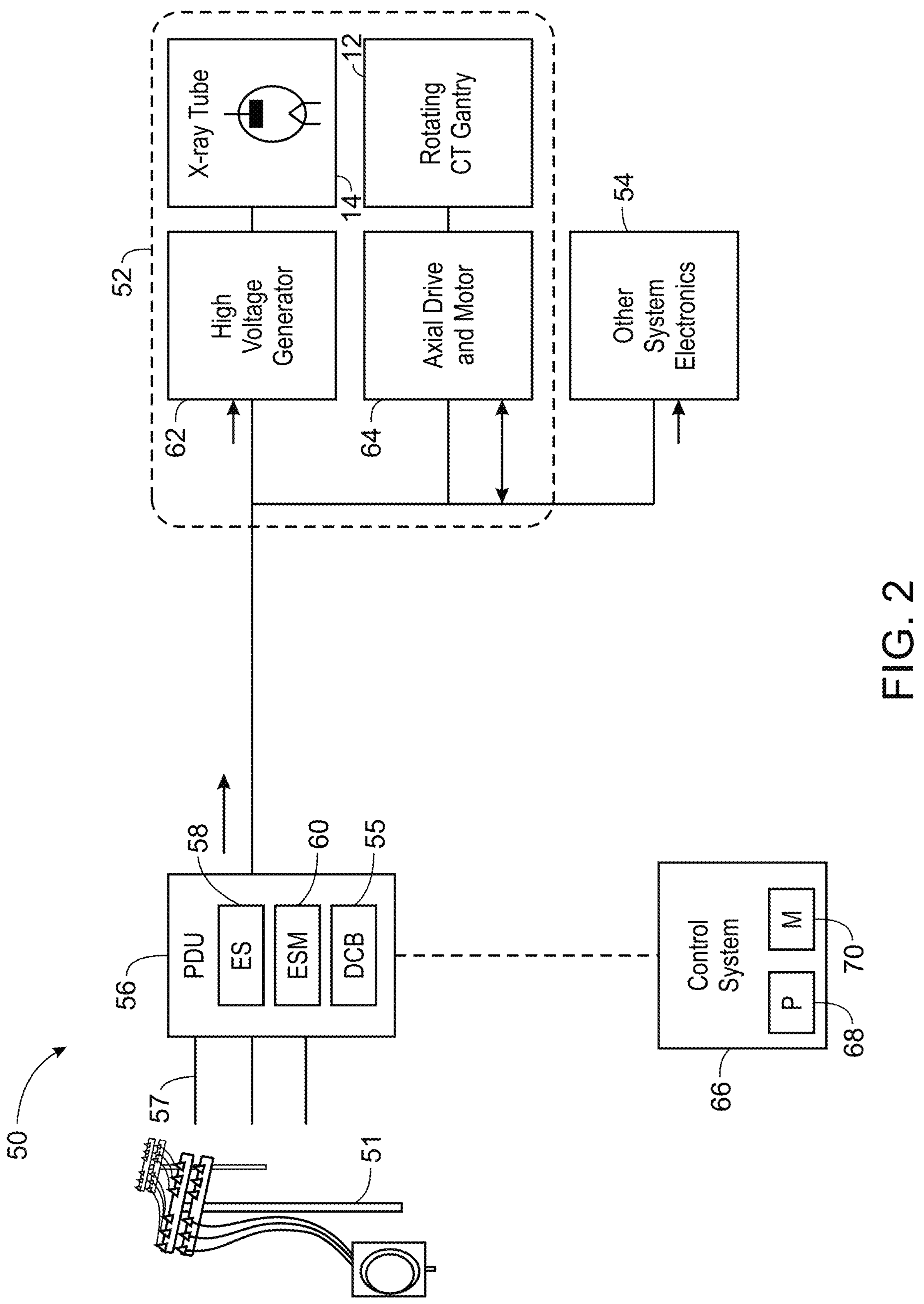
FIG. 2 is a block diagram for a medical imaging load, in accordance with aspects of the present disclosure.

FIG. 2 is discussed in the context of a computed tomography imaging system. As noted above, the disclosed embodiments can be utilized with other medical imaging systems having an X-ray source (e.g., a fluoroscopy imaging system and a radiography imaging system). FIG. 2 is a power supply system 50 that provides power to one or more medical imaging loads 52 (e.g., computed tomography imaging system 10 of FIG. 1) and/or other electronics 54 (e.g., computer 36, console 40, and/or display 42 for computed tomography imaging system 10). A main alternating current (AC) power source (e.g., from an electrical grid) may provide power (e.g., single phase or polyphase AC power such as 3-phase AC power) via an AC power line 51 to a power distribution unit (PDU) 56 via an AC input 57 (e.g., single phase or 3-phase power plug). As described in greater detail below, the power distribution unit 56 is a high efficiency power distribution unit 56 (HEPDU) having a power factor near 1.0 (0.99 or greater at a load average of 20 kilowatts or greater (kW)). The power distribution unit 56 may convert the AC power to DC power and provide the DC power to the medical imaging loads 52 and/or other electronics 54. In certain embodiments, the power distribution unit 56 also provides AC power to the medical imaging loads 52 and/or other electronics 54. As described in greater detail below, power distribution unit 56 includes an active rectifier, a passive three-phase diode bridge and two capacitors in a three-phase Vienna rectifier topology). The active rectifier enables the high efficiency power distribution unit 56 to output a constant and stabilized voltage that can be regulated. In particular, the active rectifier enables the high efficiency power distribution unit 56 to regulate HVDC voltage (e.g., DC bus voltage) at all conditions (e.g., utility sag voltage, low line condition, heavy X-ray shot, and at maximum gantry speed (e.g., 0.28 revolutions/second)). The high efficiency power distribution unit 56 is disposed outside a stationary portion of the CT imaging scanner of the system 10. Power may be transmitted from the stationary portion to a rotating portion of the CT imaging scanner of the system 10 via a slip ring or wirelessly. In certain embodiments, the high efficiency power distribution unit 56 includes a digital control board 55 for online power monitoring. The digital control board 55 is also configured for performing diagnostics offline or remotely if there is any issue on the high efficiency power distribution unit 56 or with the active rectifier. The digital control board 55 controls operation of the active rectifier. In certain embodiments, the active rectifier is communicatively coupled to a controller (e.g., controller for gantry) on the system 10 to enable the controller both to monitor and to diagnose any issues with the high efficiency power distribution unit 56. In certain embodiments, the active rectifier is communicatively coupled to the controller via an Ethernet connection (or other type of communication interface such as serial or controller area network). The system 10 may monitor and/or report on different parameters of the power supply system 50 (e.g., power distribution unit 56 including the active rectifier). These parameters may include input voltage, input current, battery voltage charge current, inverter AC voltage, inverter AC current, heat sink temperature, all board rail voltages, and other parameters. These parameters may be communicated (e.g., wired or wirelessly) from the controller to the host computer 36 and/or console 40. Besides monitoring, diagnostics may be performed on the power distribution unit 56 by the controller (via the communication interface).

The power distribution unit 56 includes an energy storage system 58 configured to store electrical power provided by the AC power line 51. In certain embodiments, the energy storage system 58 includes one or more energy storage components. For example, in certain embodiments, the energy storage system 58 may include a battery system having one or more battery banks. In certain embodiments, the energy storage components may include a plurality of batteries stacked in series. In certain embodiments, the energy storage system 58 is utilized as an uninterruptible power supply (UPS). For example, the UPS may be utilized to provide power (e.g., backup power) during operation of the CT system 10 (e.g., peak power operation).

The power distribution unit 56 also includes an energy storage management system 60 configured to manage or control the storage on and distribution of power from the energy storage system 58. In certain embodiments, the energy storage management system 60 may include a battery charger and control circuitry. In certain embodiments, the energy storage management system 60 is configured to enable storage of the electrical power on the energy storage system 58 (e.g., batteries) without pre-regulation of the electrical power. In certain embodiments, the energy storage management system 60 is configured to perform peak shaving utilizing the energy storage system 58 (e.g., during an imaging scan) by turning off power provided to the battery charger during acceleration of the gantry 12 and subsequently turning on power to the battery charger during emissions of X-rays from the X-ray source 14 (e.g., X-ray tube). In certain embodiments, the energy storage management system 60 is configured to monitor a life of the batteries of the energy storage system 58 and to provide an indication that the batteries are nearing an end of the life via a user interface. For example, the energy storage management system 60 may monitor the equivalent series resistance (ESR) of the batteries and compared it to a threshold (e.g., maximum allowable ESR value). In certain embodiments, the energy storage management system 60 may determine a charge status of the batteries and/or determine whether an imaging scan can be conducted. For example, the energy storage management system 60 may utilize the batteries for the peak power operation when there is enough charge in the batteries or, if there is not enough charge, wait to utilize the batteries for peak power operation when there is enough charge.

While one or more medical imaging loads 52 are described below with respect to loads for a computed tomography (CT) system, it will be appreciated that embodiments are applicable for use with other imaging configurations. The one or more medical imaging loads 52 may include a high voltage generator 62 coupled to the power distribution unit 56. The high voltage generator 62 may provide power to an X-ray tube 14, of the computed tomography (CT) imaging system 10. The X-ray tube 14 may emit X-ray beams toward a subject or object, such as a patient. The beam, after being attenuated by the subject, impinges upon an array of radiation detector. The intensity of the attenuated beam radiation received at the detector array may be dependent upon the attenuation of the X-ray beam by the subject. Each detector element of the detector array produces a separate electrical signal indicative of the attenuated beam received by each detector element. The electrical signals are transmitted to a data processing system for analysis which produces an image. Further, the X-ray source and the detector array may be rotated, via an axial drive and motor 64, about the gantry 12 within an imaging plane and around the subject or object. When the gantry 12 is rotated, it converts the power from the power distribution unit 56 to rotational kinetic energy via the motor 64.

The power distribution unit 56 may be controlled by a control system 66 having a FPGA or processor 68 or multiple FPGA or multiple processors and memory 70. In certain embodiments, the control system 66 is part of the power distribution unit 56 (e.g., energy storage management system 60). The processor 68 may be operatively coupled to the memory 70 to execute instructions for carrying out the presently disclosed techniques. These instructions may be encoded in programs or code stored in a tangible non-transitory computer-readable medium, such as the memory 70 and/or other storage. The processor 68 may be a general purpose processor (e.g., processor of a desktop/laptop computer), system-on-chip (SoC) device, or application-specific integrated circuit, or some other processor configuration. The memory 70, in the embodiment, includes a computer readable medium, such as, without limitation, a hard disk drive, a solid state drive, diskette, flash drive, a compact disc, a digital video disc, random access memory (RAM), and/or any suitable storage device that enables the processor 68 to store, retrieve, and/or execute instructions and/or data. The memory 70 may include one or more local and/or remote storage devices. The processor 68 may control components of the power distribution unit 56 (e.g., charger, batteries, etc.) to provide power to the one or more medical imaging loads 52.

Figure 3:
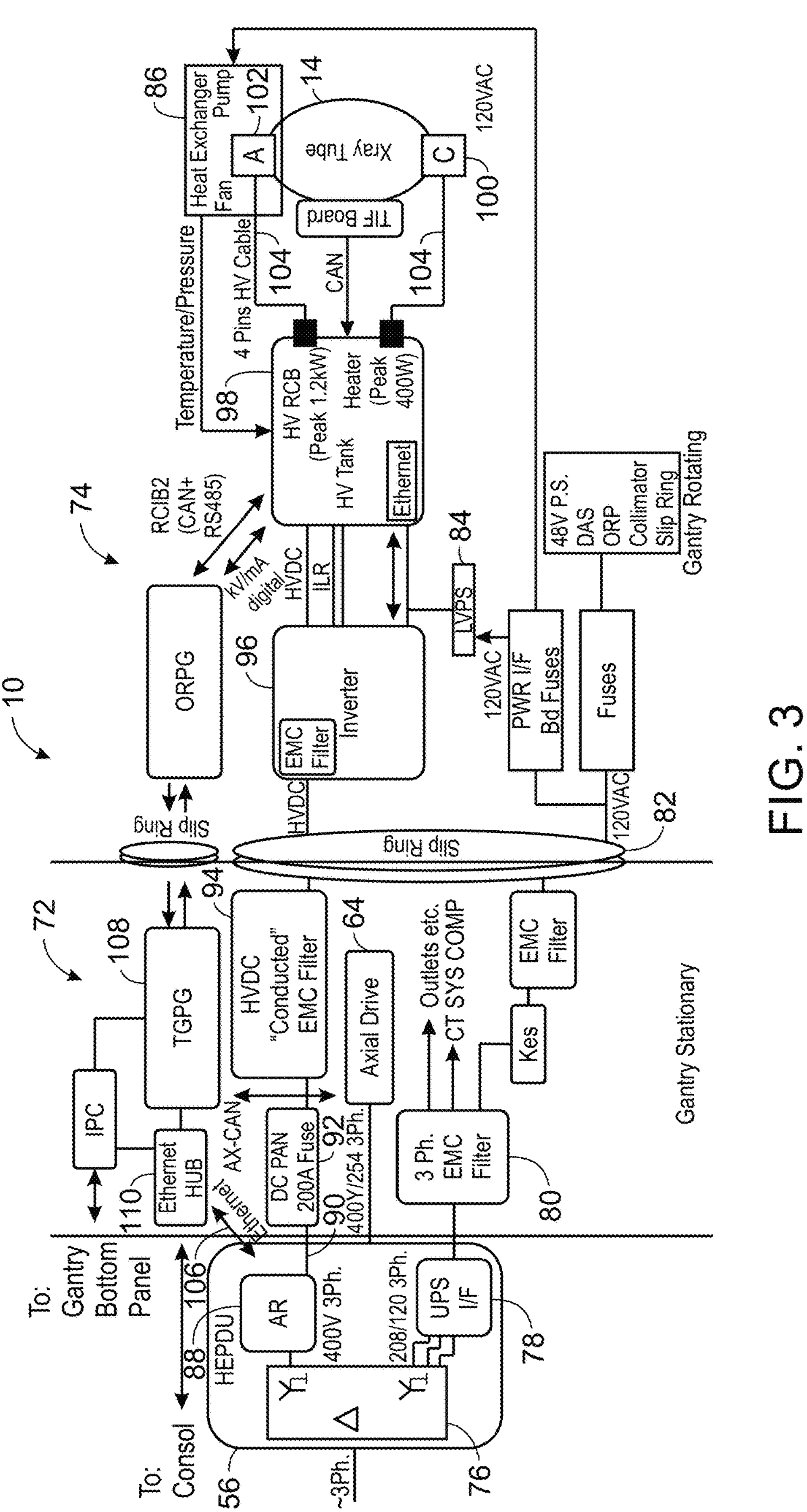
FIG. 3 is a block diagram of a power distribution unit coupled to a computed tomography imaging system, in accordance with aspects of the present disclosure.

FIG. 3 is a block diagram of the power distribution unit 56 (e.g., high efficiency power distribution unit) coupled to a computed tomography imaging system 10 (e.g., computed tomography imaging system 10 in FIG. 1). The power distribution unit 56 is configured for regulating power and providing power peak shaving to the computer tomography imaging system. It should be noted that not all components of the power distribution unit 56 are shown.

The computed tomography imaging system 10 includes a stationary gantry portion 72 and a rotating gantry portion 74. The power distribution unit 56 is located outside the stationary gantry portion 72. The power distribution unit 56 includes a transformer 76 (e.g., three-phase isolation transformer) configured to receive power (e.g., three-phase alternating current (AC)) from an electrical grid (e.g., utility grid).

The power distribution unit 56 includes an uninterrupted power supply (UPS) interface 78 coupled to the transformer 76 that provides power (e.g., AC power) to various components of the stationary gantry portion 72 of the computed tomography imaging system 10. For example, one phase of 120/208Y three-phase secondary is utilized to power, via the UPS interface 78, provides power the service outlets, gantry heater, and other components. The other phases of the 120/208Y three-phase secondary are utilized to power the CT system computers. A three-phase electromagnetic compatibility (EMC) filter 80 is disposed downstream of the UPS interface 78 within the stationary gantry portion 72 and configured to keep an electromagnetic disturbance from occurring or impacting the equipment powered via the UPS interface 78. Power (e.g., 120V AC) provided by the UPS interface 78 is also transmitted from stationary gantry portion 72 to the rotating gantry portion 74 via a slip ring 82 to power a low voltage power supply 84 (e.g., 48V), a heat exchanger 86 associated with the X-ray tube 14, and other system components (e.g., table gantry, gantry rotating parts, etc.). The 254/440Y three-phase secondary from the transformer 76 is utilized to power the axial drive and motor 64 on the stationary gantry portion 72.

The power distribution unit 56 also includes an active rectifier (AR) 88. The transformer 76 inputs AC power into the active rectifier 88. The active rectifier 88 outputs DC power (e.g., HVDC voltage or DC bus voltage at 700 or 800 Vdc −50/+20V as example). Via line 90, the power is provided to the stationary gantry portion 72 and passes through a fuse 92 (e.g., DC pan 200A fuse) and HVDC conducted EMC filter 94. Power along line 90 is transmitted to the rotating gantry portion 74 via the slip ring 82. On the rotating gantry portion 74, the power passes through an inverter 96 and is provided to a high voltage tank 98. The high voltage tank 98 is coupled to and provides a high voltage potential difference between a cathode assembly 100 and an anode assembly 102 of the X-ray tube 14. The high voltage tank 98 is coupled to the cathode assembly 100 and the anode assembly 102 via high voltage cables 104.

The active rectifier 88 enables the high efficiency power distribution unit 56 to output a constant and stabilized voltage that can be regulated. In particular, active rectifier 88 enables the high efficiency power distribution unit to regulate HVDC voltage (e.g., DC bus voltage) at all conditions (e.g., utility sag voltage, low line condition, heavy X-ray shot, and at maximum gantry speed). In certain embodiments, the active rectifier 88 includes a passive three-phase diode bridge and two capacitors in a three-phase Vienna rectifier topology. The use of the active rectifier 88 by the high efficiency power distribution unit 56 also enables the power factor of the high efficiency power distribution unit 56 to be close to 1.0 (e.g., 0.99 or greater) at all conditions. In particular, the absence of a harmonic current enables the high efficiency power distribution unit to be more efficient.

The active rectifier 88 allow direct connection to worldwide three-phase AC main power (e.g., 380-480V±10 percent). The active rectifier 88 provides an adjustable voltage output at 700 or 800 Vdc −50/+20V. The active rectifier 88 is configured to provide a maximum peak output power of 150 KW and 20 kW average output power. The active rectifier 88 provides full dynamic power capability that is robust until 300 μH 0.12 ohm line impedance. The active rectifier provides both a power factor 0.99 or greater and efficiency of 0.96 or greater at full power. The active rectifier 88 is configured to monitor the main power. In addition, the active rectifier 88 is includes a communication interface to communicate (e.g., via Ethernet), as indicated by arrow 106, with a controller 108 (e.g., controller for gantry (TGPG)) on the system 10, via an Ethernet hub 110, to enable the controller 108 to monitor and to diagnose any issues (e.g., faults) with the high efficiency power distribution unit 56 (and the active rectifier 88).

Figure 4:
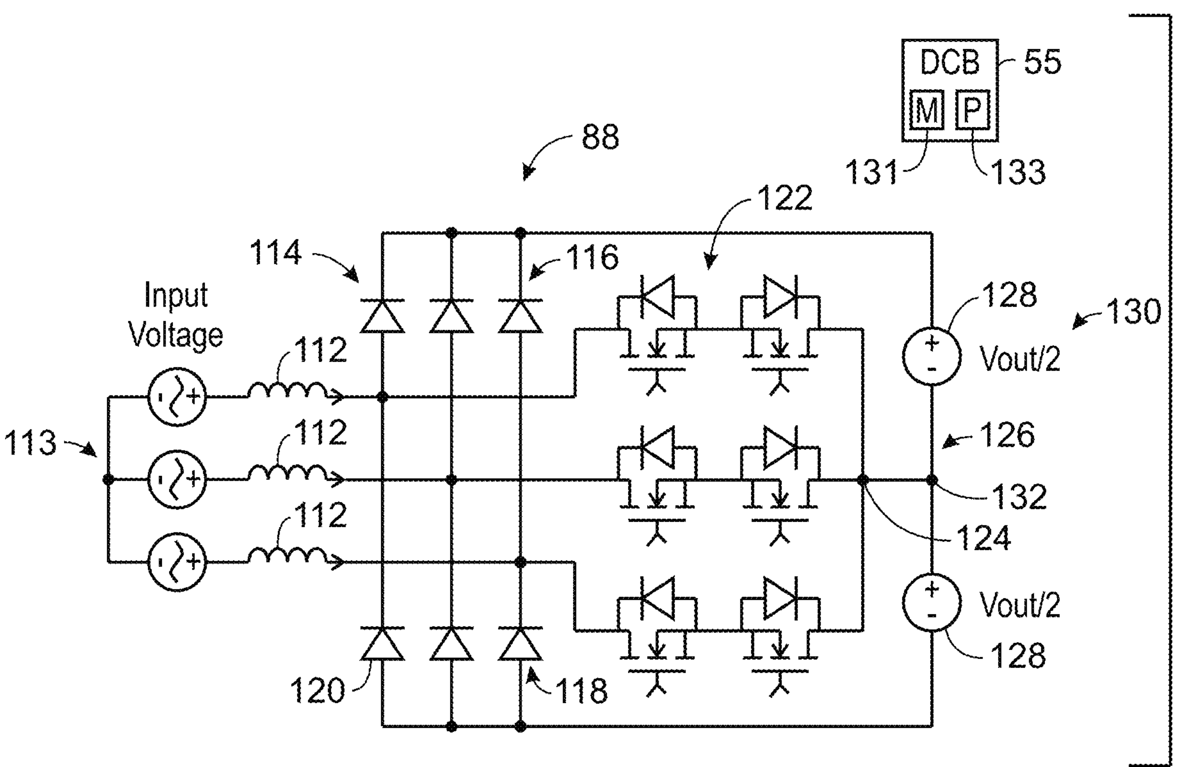
FIG. 4 is a schematic diagram of an active rectifier in a three-phase Vienna topology, in accordance with aspects of the present disclosure.

FIG. 4 is a schematic diagram of the active rectifier 88 in a three-phase Vienna topology. As depicted, the active rectifier 88 includes coupled inductors 112 at three different phases located on an input side 113. On input side 113, the active rectifier 88 receives an input voltage (e.g., three-phase AC power). The active rectifier 88 also includes a passive three-phase diode bridge 114 with both an upper bridge section 116 and a lower bridge section 118 having three diodes 120. The active rectifier 88 further includes a section 122 of IGBTs and diodes wherein the switches (e.g., power semiconductors) connect the three phases at a star point 124. The active rectifier 88 further includes a DC-link 126 that includes a pair of DC-link capacitors 128 located on an output side 130. A center tap 132 located between the pair of DC-link capacitors 128 is connected to the star point 124. An output voltage (e.g., DC power) is outputted from the active rectifier 88 (e.g., tapped off via the DC-link 126).

The active rectifier 88 is controlled by the digital control board 55 (e.g., active rectifier controller). The digital control board 55 may be configured to utilize IP control. In particular, an internal state machine may be utilized to control the active rectifier 88. The digital control board 55 is configured to start the function of the active rectifier 88 as soon as main voltage is present. The digital control board 55 is configured to monitor the three-phase input (e.g., for grid monitoring purposes) when not regulating the DC bus voltage (e.g., between examinations). The digital control board 55 is configured to provide test modes to enable operation of the IGBT gate drivers, the output relays, and analog to digital converter channels. The digital control board 55 is also configured to detect errors. For example, the digital control board 55 may detect fatal errors (e.g., malfunction that could damage hardware). Examples of conditions for triggering detection of fatal errors include the voltage on the output capacitors being above an error limit (i.e., too high), the output voltage being too low, or a gate fuse being blown. Also, the digital control board 55 may detect critical errors (e.g., an anomaly that imposes a stop of operation of the active rectifier 88). Further, the digital control board 55 may detect a warning condition and send an event warning. Examples of conditions for triggering warnings includes the output voltage being too high, the output voltage being too low, the phase currents being high, the DC bus current being too high, and the difference between the output capacitor voltages being unbalanced.

The digital control board 55 includes a memory 131 encoding processor-executable routines or code. The digital control board 55 also includes a processor 133 configured to access the memory 131 and to execute the processor-executable routines, wherein the processor-executable routines, when executed by the processor 133, cause the processor to perform actions. As an example, the memory 131 may store processor-executable software code or instructions (e.g., firmware or software), which are tangibly stored on a non-transitory computer readable medium. Additionally or alternatively, the memory 131 may store data. As an example, the memory 131 may include a volatile memory, such as random access memory (RAM), and/or a nonvolatile memory, such as read-only memory (ROM), flash memory, a hard drive, or any other suitable optical, magnetic, or solid-state storage medium, or a combination thereof. Furthermore, the processor 133 may include multiple microprocessors, one or more "general-purpose" microprocessors, one or more special-purpose microprocessors, and/or one or more application specific integrated circuits (ASICS), or some combination thereof. For example, the processor 133 may include one or more reduced instruction set (RISC) or complex instruction set (CISC) processors. The processor 133 may include multiple processors, and/or the memory 131 may include multiple memory devices.

During the monitoring of the main power network, the digital control board 55 is configured to detect and report power quality events (e.g., when the measured main voltage is outside the specifications). In certain embodiments, the digital control board 55 may detect a main power interruption prior to the CT system detecting it. In this scenario, the digital control board 55 is configured to stop X-ray exposures and change the rotation speed of the gantry. In addition, DC bus discharging circuit is available to discharge HVDC for less than 1 minute for safety. If the interruption is detected by the CT system, a control signal may be sent to the digital control board (e.g., via Ethernet) to switch to a particular type of UPS.

Although in the preferred embodiment, the three-phase Vienna rectifier is utilized as the active rectifier 88. The active rectifier 88 for the high efficiency power distribution unit 56 may utilize other active front-end topologies. For example, the active rectifier 88 may be a two-level inverter or a six pulse boost rectifier.

Figure 5:
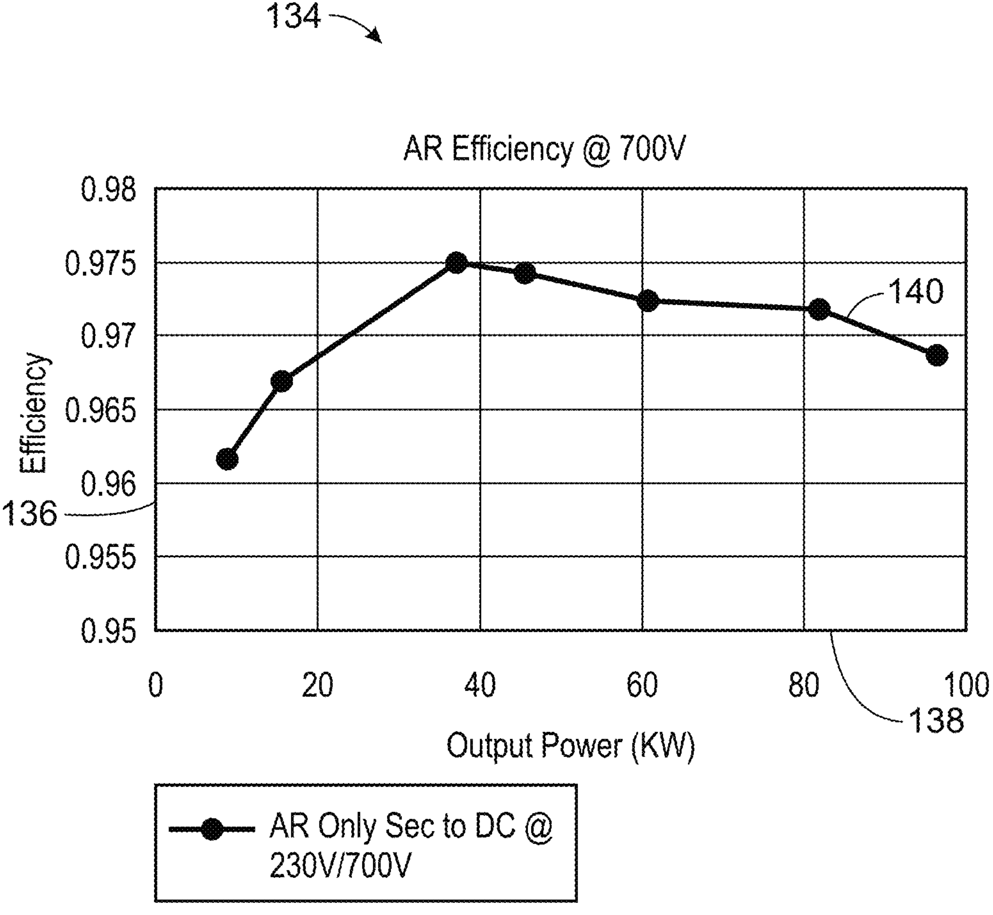
FIG. 5 is a graph illustrating an efficiency of an active rectifier, in accordance with aspects of the present disclosure.

FIG. 5 is a graph 134 illustrating an efficiency of the active rectifier (e.g., three-phase Vienna rectifier). The graph 134 includes a y-axis 136 representing efficiency. The graph 134 includes an x-axis 138 representing output power (in kilowatts). Plot 140 represents the efficiency of the active rectifier at 700V. As depicted, the efficiency of the active rectifier is greater than 0.96 across different levels of output power.

Figure 6:
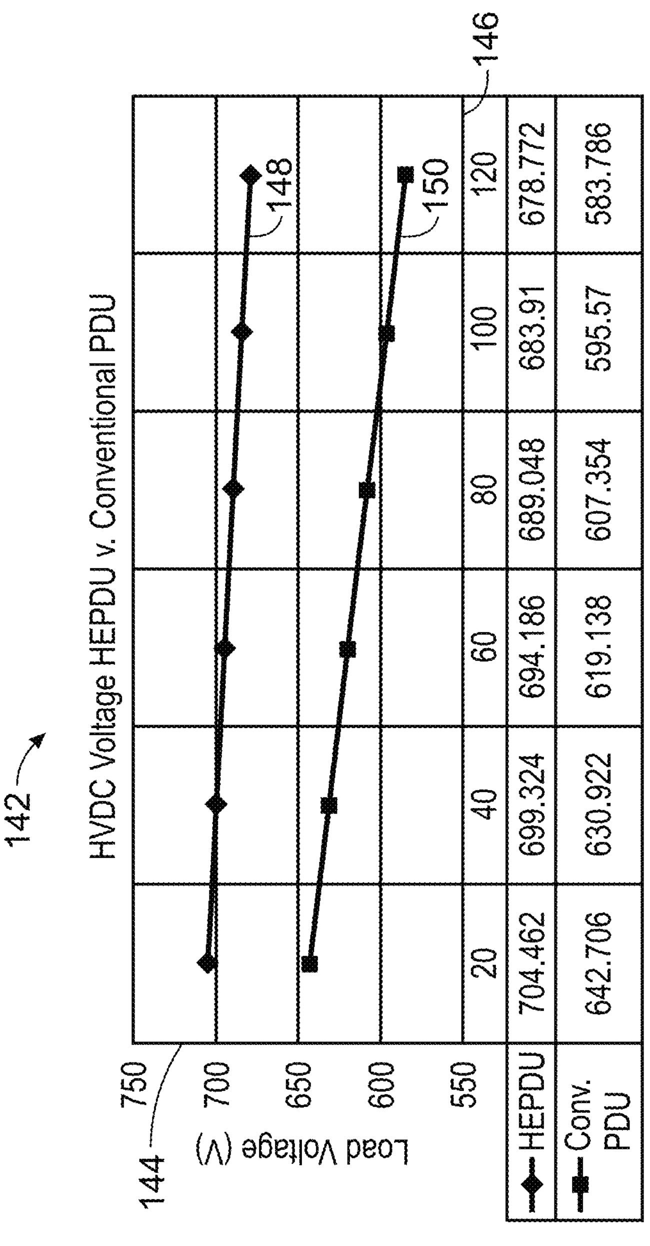
FIG. 6 is a graph comparing high voltage direct current voltage (HVDC) of a high efficiency power distribution unit versus a conventional power distribution unit at different load conditions, in accordance with aspects of the present disclosure.

FIG. 6 is a graph 142 comparing high voltage direct current voltage (HVDC) of a high efficiency power distribution unit (e.g., having active rectifier as described above) versus a conventional power distribution unit (e.g., having a passive rectifier). The graph 142 includes a y-axis 144 representing load voltage. The graph 142 also includes an x-axis 146 representing different loads (e.g., 20 kW, 40 kW, 60 kW, 80 kW, 100 KW, and 120 kW). Plot 148 represents the load voltage at the different loads outputted by the high efficiency power distribution unit. Plot 150 represents the load voltage at the different loads outputted by the conventional power distribution unit. As depicted, the high efficiency power distribution outputs a greater voltage at the different loads compared to the conventional power distribution unit.

Figure 7:
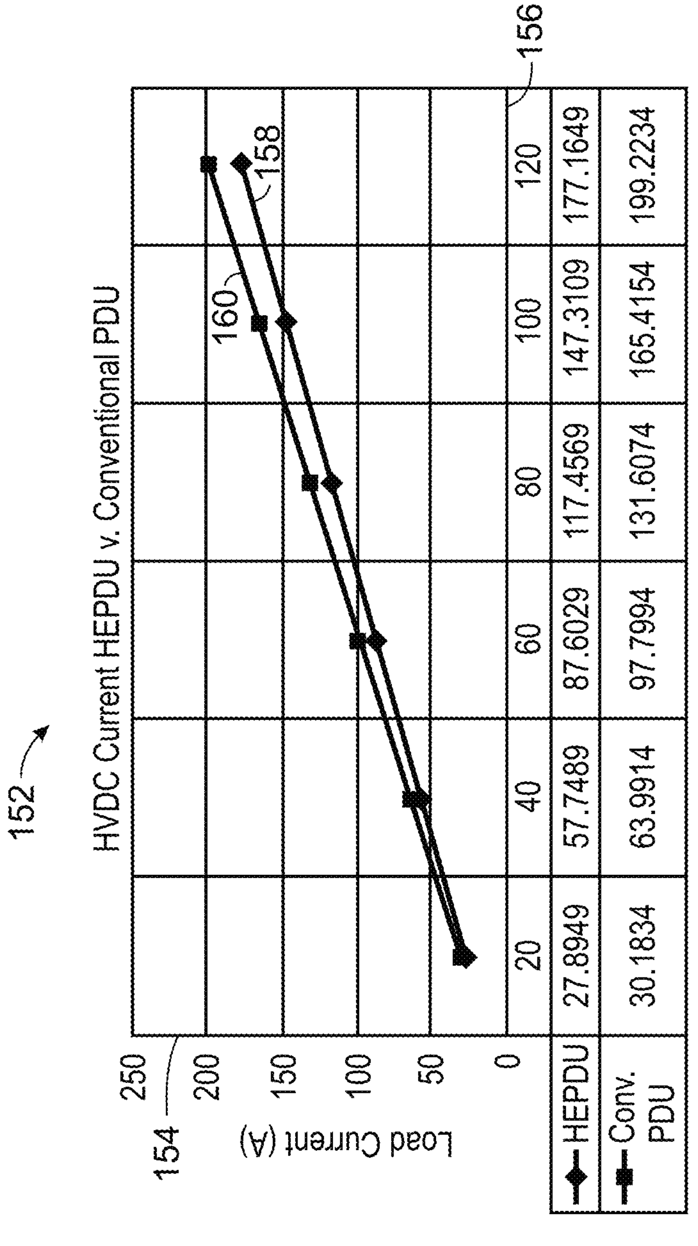
FIG. 7 is a graph comparing HVDC current of a high efficiency power distribution unit versus a conventional power distribution unit at different load conditions, in accordance with aspects of the present disclosure.

FIG. 7 is a graph 152 comparing HVDC current of a high efficiency power distribution unit (e.g., having active rectifier as described above) versus a conventional power distribution unit (e.g., having a passive rectifier). The graph 152 includes a y-axis 154 representing load current. The graph 152 also includes an x-axis 156 representing different loads (e.g., 20 kW, 40 kW, 60 kW, 80 kW, 100 kW, and 120 kW). Plot 158 represents the load current at the different loads outputted by the high efficiency power distribution unit. Plot 160 represents the load current at the different loads outputted by the conventional power distribution unit. As depicted, the high efficiency power distribution outputs a lower current at the different loads compared to the conventional power distribution unit.

Figure 8:
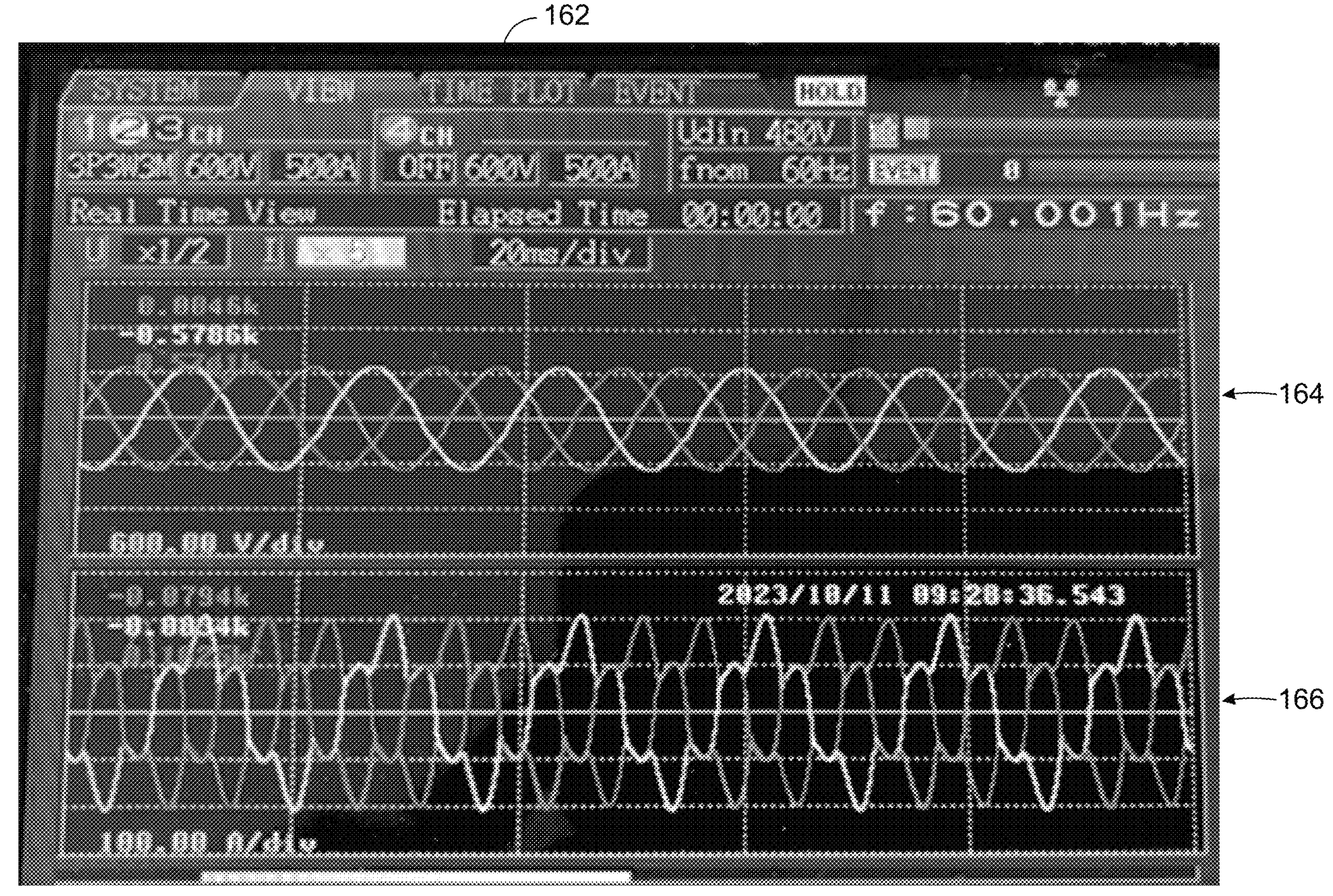
FIG. 8 depicts an image of input voltage and input current waveforms at a particular load condition for a conventional power distribution unit.

FIG. 8 depicts an image 162 of input voltage and input current waveforms at a particular load condition for a conventional power distribution unit (e.g., having a passive rectifier). A top portion 164 of the image 162 depicts the input voltage waveform for the conventional power distribution unit at the particular load condition. A bottom portion 166 of the image 162 depicts the input current waveform for the conventional power distribution unit at the particular load condition. As depicted, the input current waveform is not sinusoidal. Thus, the conventional power distribution unit will have more harmonic currents which will generate more heat in the conventional power distribution unit transformer. Also, the power factor will be lower for the conventional power distribution unit.

Figure 9:
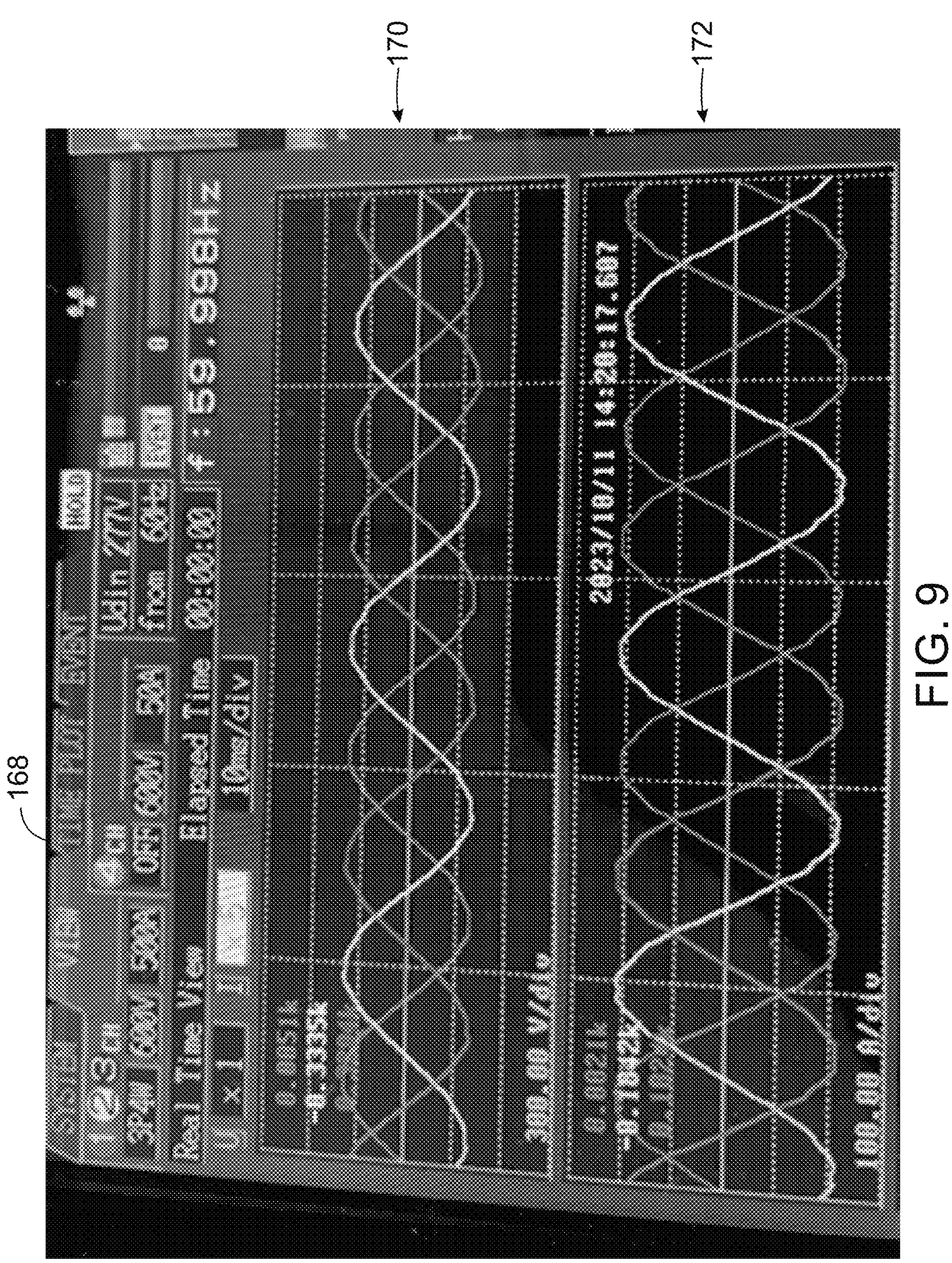
FIG. 9 depicts an image of input voltage and input current waveforms at a particular load (same load condition for the conventional power distribution unit in FIG. 8) for a high efficiency power distribution unit, in accordance with aspects of the present disclosure.

FIG. 9 depicts an image 168 of input voltage and input current waveforms at a particular load condition (e.g., same load condition utilized for the conventional power distribution unit in FIG. 8) for a high efficiency power distribution unit (e.g., having an active rectifier as described above). A top portion 170 of the image 168 depicts the input voltage waveform for the high efficiency power distribution unit at the particular load condition. A bottom portion 172 of the image 168 depicts the input current waveform for the high efficiency power distribution unit at the particular load condition. As depicted, the input current waveform is sinusoidal. Thus, the high efficiency power distribution unit will generate less heat in the power transformer compared to the conventional power distribution unit. Also, the power factor will be higher for the high efficiency power distribution unit compared to the conventional power distribution unit. Indeed, the power factor for the high efficiency power distribution unit will be near 1.00 (e.g., 0.99 or greater).

Figure 10:
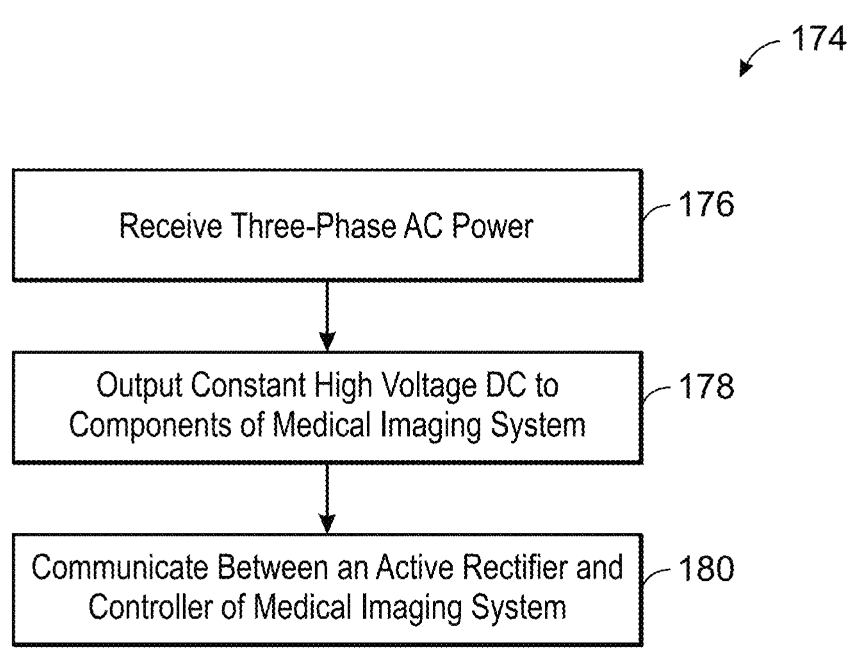
FIG. 10 is flowchart of a method for regulating use of electrical power by a medical imaging system including an X-ray source configured to emit X-rays, in accordance with aspects of the present disclosure.

FIG. 10 is flowchart of a method 174 for regulating use of electrical power by a medical imaging system including an X-ray source configured to emit X-rays. One or more steps of the method 174 may be performed simultaneously and/or in a different order from that depicted in FIG. 10. The method 174 may be performed by one or more components of the high efficiency power distribution unit 56 in FIG. 2 (e.g., active rectifier, digital control board, etc.). The medical imaging system may be a computed tomography imaging system, a fluoroscopy imaging system, and a radiography imaging system (i.e., conventional imaging system including a mammography imaging system).

The method 174 includes receiving, at a high efficiency power distribution unit for the medical imaging system, three-phase alternating current power from an electrical grid (block 176). The method 174 also includes outputting, from the high efficiency power distribution unit, a constant high voltage direct current to components of the medical imaging system including a high voltage generator configured to provide power to the X-ray source. The power distribution unit includes an active rectifier that regulates the high voltage direct current, wherein the active rectifier comprises a passive three-phase diode bridge and two capacitors in a three-phase Vienna rectifier topology (block 178). the active rectifier is configured to enable the high efficiency power distribution unit to output a constant high voltage direct current. In certain embodiments, the active rectifier includes a passive three-phase diode bridge and two capacitors. In certain embodiments, the active rectifier is configured to regulate the high voltage direct current provided to the high voltage generator under all conditions. In certain embodiments, the conditions include utility sag voltage, low line condition, heavy X-ray shot, and at maximum gantry speed. In certain embodiments, the high efficiency power distribution unit has a power factor of 0.99 or greater at all conditions.

The method 174 further includes communicating between an active rectifier and a controller on the medical imaging system to enable the controller both to monitor and to diagnose any issues with the high efficiency power distribution unit (block 180). In certain embodiments, the active rectifier is communicatively coupled to the controller of the medical imaging system via an Ethernet connection.

Technical effects of the disclosed embodiments include providing a high efficiency power distribution unit for a medical imaging system including an X-ray source configured to emit X-rays. The medical imaging system may be a computed tomography imaging system, a fluoroscopy imaging system, and a radiography imaging system (i.e., conventional imaging system including a mammography imaging system). Technical effects of the disclosed embodiments include utilizing an active rectifier to enable the high efficiency power distribution unit to output a constant and stabilized voltage that can be regulated. In particular, active rectifier enables the high efficiency power distribution unit to regulate HVDC voltage (e.g., DC bus voltage) at all conditions (e.g., utility sag voltage, low line condition, heavy X-ray shot, and at maximum gantry speed). This enables the sizes of switches and heat sink to be reduced. This also increases the efficiency of the X-ray generator inverter. Technical effects of the disclosed embodiments further include enabling the manufacturing of a much smaller and cheaper (e.g., approximately 30 percent less) X-ray generator. Technical effects of the disclosed embodiments include enabling the power factor of the high efficiency power distribution unit to be close to 1.0 (e.g., 0.99 or greater) at all conditions. In particular, the absence of a harmonic current enables the high efficiency power distribution unit to be more efficient. This results in a reduction in the site utility power range and an increase in cost savings (e.g., due to energy saving). Technical effects of the disclosed subject matter includes increasing the efficiency of the medical imaging system (e.g., computed tomography imaging system). The higher power factor also either enables a smaller Mains plug rating or higher available power.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
- an X-ray source configured to emit X-rays;
- a high voltage generator configured to provide power to the X-ray source; and
- a high efficiency power distribution unit configured to receive electrical power from an electrical grid and to store the electrical power, wherein the high efficiency power distribution unit comprises an active rectifier configured to regulate a high voltage direct current outputted to components of the medical imaging system including the high voltage generator, and wherein the active rectifier is configured to regulate the high voltage direct current provided to the high voltage generator under all conditions.

2. The medical imaging system of claim 1, wherein the active rectifier is configured to enable the high efficiency power distribution unit to output a constant high voltage direct current.

3. The medical imaging system of claim 1, wherein the active rectifier comprises a passive three-phase diode bridge and two capacitors.

4. The medical imaging system of claim 3, wherein the active rectifier comprises a three-phase Vienna rectifier topology.

5. The medical imaging system of claim 1, wherein the conditions comprise utility sag voltage, low line condition, heavy X-ray shot, and at maximum gantry speed.

6. The medical imaging system of claim 1, wherein the high efficiency power distribution unit has a power factor of 0.99 or greater at all conditions including a high power condition.

7. The medical imaging system of claim 1, wherein the active rectifier is communicatively coupled to a controller located on a gantry of the medical imaging system to enable the controller both to monitor and to diagnose any issues with the high efficiency power distribution unit.

8. The medical imaging system of claim 7, wherein the active rectifier is communicatively coupled to the controller via an Ethernet connection.

9. The medical imaging system of claim 1, wherein the medical imaging system comprises a computed tomography imaging system.

10. A high efficiency power distribution unit for a medical imaging system comprising an X-ray source configured to emit X-rays, comprising:
- an active rectifier configured to regulate a high voltage direct current outputted to components of the medical imaging system including a high voltage generator configured to provide power to the X-ray source, wherein the active rectifier is configured to enable the high efficiency power distribution unit to output a constant high voltage direct current, and wherein the high efficiency power distribution unit is configured to receive electrical power from an electrical grid and to store the electrical power, and wherein the active rectifier is configured to regulate the high voltage direct current provided to the high voltage generator under all conditions.

11. The high efficiency power distribution unit of claim 10, wherein the active rectifier comprises a passive three-phase diode bridge and two capacitors.

12. The high efficiency power distribution unit of claim 11, wherein the active rectifier comprises a three-phase Vienna rectifier topology.

13. The high efficiency power distribution unit of claim 10, wherein the conditions comprise utility sag voltage, low line condition, heavy X-ray shot, and at maximum gantry speed.

14. The high efficiency power distribution unit of claim 10, wherein the active rectifier is configured to be communicatively coupled to a controller located on a gantry of the medical imaging system to enable the controller both to monitor and to diagnose any issues with the high efficiency power distribution unit.

15. The high efficiency power distribution unit of claim 14, wherein the active rectifier is configured to be communicatively coupled to the controller via an Ethernet connection.

16. The high efficiency power distribution unit of claim 10, wherein the medical imaging system comprises a computed tomography imaging system.

17. A method for regulating use of electrical power by a medical imaging system comprising an X-ray source configured to emit X-rays, comprising:
- receiving, at a high efficiency power distribution unit for the medical imaging system, three-phase alternating current power from an electrical grid; and outputting, from the high efficiency power distribution unit, a constant high voltage direct current to components of the medical imaging system including a high voltage generator configured to provide power to the X-ray source, wherein the high efficiency power distribution unit comprises an active rectifier that regulates the high voltage direct current, wherein the active rectifier comprises a passive three-phase diode bridge and two capacitors in a three-phase Vienna rectifier topology, and wherein the active rectifier is configured to regulate the constant high voltage direct current provided to the high voltage generator under all conditions.

18. The method of claim 17, wherein the medical imaging system comprises a computed tomography imaging system.

* * * * *